(12) United States Patent
Krema et al.

(10) Patent No.: US 7,006,600 B1
(45) Date of Patent: Feb. 28, 2006

(54) INTEGRATED DIGITAL DENTAL X-RAY SYSTEM

(75) Inventors: Alan P. Krema, Naperville, IL (US); George Stantchev, Phoenix, AZ (US); Lyubomir Cekov, Schamburg, IL (US); Mark Greenwood, Deer Park, IL (US)

(73) Assignee: Progeny, Inc., Buffalo Grove, IL (US)

( * ) Notice: Subject to any disclaimer, the term of this patent is extended or adjusted under 35 U.S.C. 154(b) by 80 days.

(21) Appl. No.: 10/758,682

(22) Filed: Jan. 15, 2004

(51) Int. Cl.
H05G 1/64 (2006.01)

(52) U.S. Cl. .................................... 378/98.7

(58) Field of Classification Search ................ 378/96, 378/97, 98.7, 108, 168
See application file for complete search history.

(56) References Cited

U.S. PATENT DOCUMENTS

| | | | |
|---|---|---|---|
| 2,798,958 A * | 7/1957 | Hudson et al. | 378/39 |
| 5,331,166 A | 7/1994 | Crosetto et al. | |
| 5,426,684 A * | 6/1995 | Gaborski et al. | 378/98 |
| 5,510,623 A | 4/1996 | Sayag et al. | |
| 5,513,252 A | 4/1996 | Blaschka et al. | |
| 5,671,738 A | 9/1997 | Thornberg | |
| 5,694,448 A | 12/1997 | Morcom | |
| 5,694,449 A * | 12/1997 | Aragones | 378/115 |
| 5,744,806 A | 4/1998 | Frojd | |
| 5,784,429 A | 7/1998 | Arai | |
| 5,784,434 A | 7/1998 | Shieh | |
| 5,828,726 A | 10/1998 | Polichar et al. | |
| 5,912,942 A | 6/1999 | Schick et al. | |
| 6,002,742 A | 12/1999 | Nelvig | |
| 6,069,935 A | 5/2000 | Schick et al. | |
| 6,148,060 A | 11/2000 | Collins et al. | |
| 6,236,712 B1 * | 5/2001 | Tomasetti et al. | 378/114 |
| 6,272,204 B1 | 8/2001 | Amtower et al. | |
| 6,404,854 B1 * | 6/2002 | Carroll et al. | 378/98 |
| 2002/0015283 A1 * | 2/2002 | Sallam | 361/681 |

* cited by examiner

*Primary Examiner*—Edward J. Glick
*Assistant Examiner*—Chih-Cheng Glen Kao
(74) *Attorney, Agent, or Firm*—Nicholas A Kees; Godfrey & Kahn, S.C.

(57) ABSTRACT

An integrated digital x-ray diagnostic system and a method for conducting dental radiography which includes optimizing exposure settings based on certain physical parameters of a patient, communicating the operational status of the x-ray generator and the exposure settings directly to the a CCD sensor without radiation sensitive detector elements, and supplying various viewing stations with image data thereby improving dental office workflow. The activation of the sensor and the x-ray source are coordinated so as to avoid pre-integration of charge in the image sensor, and at the same time reduce risk of over-exposure to the patient.

20 Claims, 4 Drawing Sheets

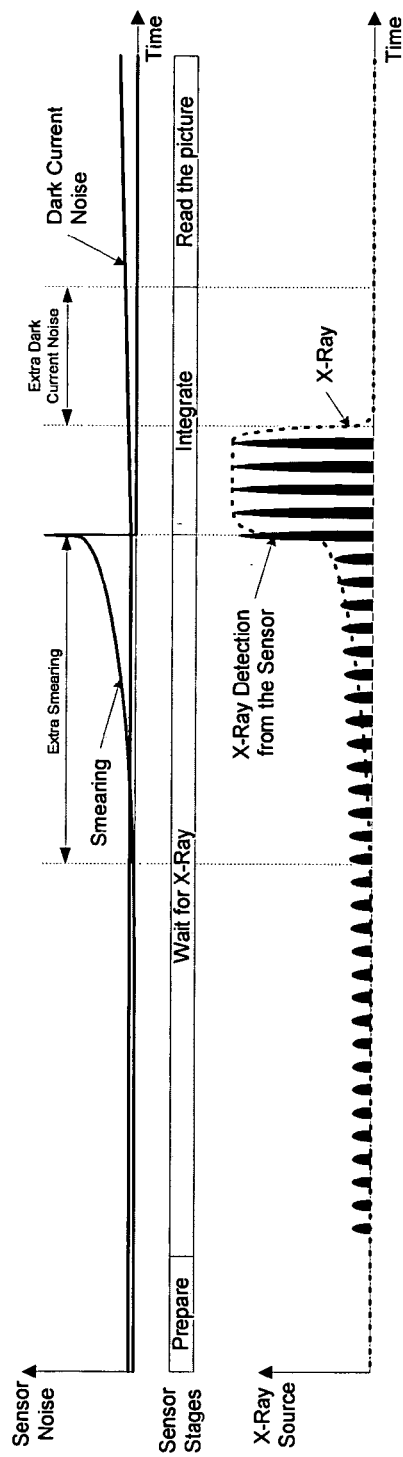
PRIOR ART    FIG. 4
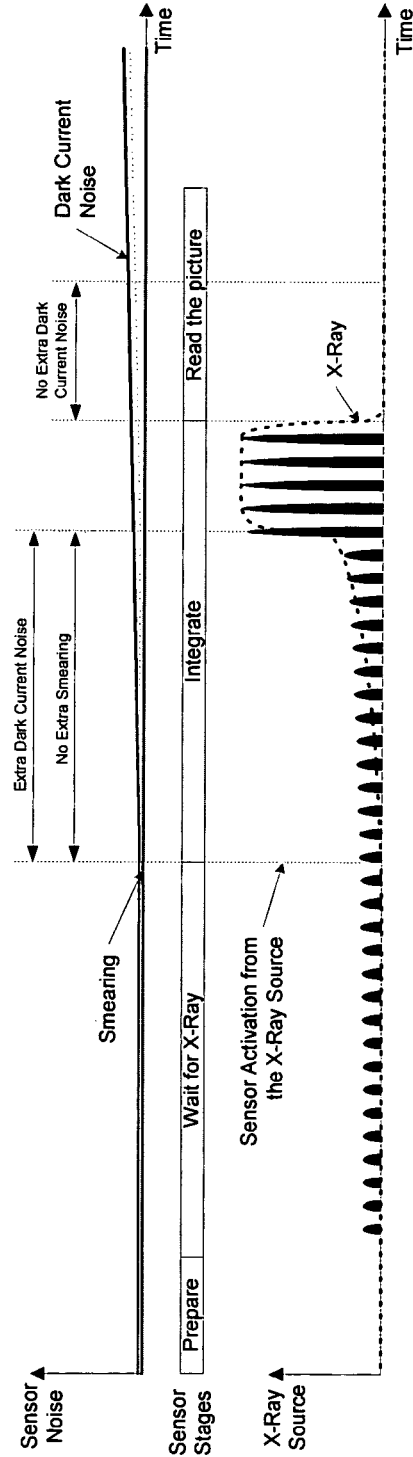
FIG. 5

INTEGRATED DIGITAL DENTAL X-RAY SYSTEM

BACKGROUND OF THE INVENTION

The present invention relates to an integrated digital x-ray diagnostic system and a method for conducting dental radiography which includes optimizing exposure settings based on certain physical parameters of a patient, communicating the operational status of the x-ray generator and the exposure settings directly to a CCD sensor without radiation sensitive detector elements, and supplying various viewing stations with image data thereby improving dental office workflow.

Digital image detectors, such as CCD sensors used in conventional video cameras, have been adapted to be x-ray sensitive elements in dental x-ray applications. For the past few decades, CCD sensors have been established as a leading technology in high-performance digital x-ray imaging. Unlike matrix-addressed sensors like amorphous silicon panels and CMOS imagers, CCD sensors read out their signal by transporting charge packets across their silicon substrate. The advantages of using a CCD sensor in conjunction with a typical digital x-ray diagnostic system often include high resolution and sensitivity, low noise and reduced radiation loads. Examples of inventions using CCD-type sensors in dental environments are described in U.S. Pat. Nos. 5,513,252, 5,784,429, and 6,002,742.

Methods and devices used for triggering the activation and/or deactivation of the x-ray generator used in connection with a CCD sensor vary widely in the art. Generally, most dental x-ray diagnostic systems used today incorporate sensing elements disposed in or around the CCD image sensor. These configurations allowed companies to manufacture just the x-ray sensing components of the system, and then sell those components to dentists, who would then combine them with x-ray generation units already installed in the dental offices. Such a componentized approach reduced the cost of the new equipment and therefore may have facilitated the overall industry shift from film-based radiography to digital diagnostics. It has also, however, led to significant technical limitations in the art.

In one known arrangement, one or more supplementary x-ray sensing elements are located close to the imaging area to detect the start and end of the x-ray pulse. Such an arrangement is disclosed in Crosetto, et al, U.S. Pat. No. 5,331,166. A signal is sent from the supplementary sensing element to the control circuitry of the image sensor to control image acquisition. The use of supplementary sensing elements adds size and complexity to the image sensor arrangement. The supplementary sensing elements also have to cover a significant part of the image area to minimize the risk of being shaded by a dense part of the object to be imaged.

In another arrangement, Sayag, et al., U.S. Pat. No. 5,510,623, the image sensor itself is continuously read out while waiting for exposure. The signal, either from one pixel or summed from many pixels, is compared to a fixed or variable threshold to determine the onset of radiation. This method as used with, for example, CCD sensors, requires shifting of the image along the sensor. The disadvantage of this method is the need of precise amplitude and timing for the shifting clocks in order to avoid loss of signal and image smearing.

Nelvig, U.S. Pat. No. 6,002,742, describes an arrangement where, in one embodiment, in-coming radiation is sensed by the use of several sensing diodes positioned at the back of the CCD device. Once radiation is sensed, the x-ray source is triggered to deactivate. In another embodiment, the CCD itself acts as the sensing medium by utilizing a multitude of charging pixel capacitors within the CCD device itself. However, both Nelvig embodiments require clocking the CCD cell by a logic device to determine the length and dose of the radiation. Additionally, both embodiments do not utilize customized exposure times calculated based on varying categories of teeth (i.e. incisors, canines, pre-molars and molars), and most importantly, varying anatomies of the patient (adult or child). This lack of tailored exposure settings may increase the risk of over-exposing children.

Schick, et al., U.S. Pat. No. 5,912,942, and Schick et al., U.S. Pat. No. 6,069,935, a continuation of the former, describe an x-ray detector with a scintillator that converts the x-ray energy into an electrical signal by using CMOS active pixel array sensor. Using CMOS sensors allows simple, low cost and low power solutions. The main disadvantages are the lower dynamic range, high pattern noise, lower resolution, high dark current and fair quantum efficiency compared with the CCD image sensors.

Finally, all of the above arrangements require the CCD to be in a perpetual charged state because they are in constant anticipation of incoming radiation. The charged CCDs lead to heightened noise accumulation along an unregulated exposure integration cycle, which detrimentally affects the quality of the resultant image.

Methods for displaying digital images after they have been captured have also taken many forms in the known art. Generally, a personal computer electronically attached to the image sensor itself or to an image processing unit is the most commonly employed technique in the art. Typically, a display computer is placed in a separate office where it can be manipulated away from the x-ray source so as to limit the amount of radiation exposure experienced by dental office employees. There are also provisions for presenting images on a display located adjacent a dentist's chair, facilitating viewing of the captured x-ray image(s) by doctor and patient alike. This arrangement typically involves an additional presentation/processing unit, as indicated above, located out of range of the x-ray source. However, there are obvious drawbacks in having stationary and remote display arrangements, the most evident being the disruption in the efficiency of dental office workflow. Before an image can be viable for diagnosis, or in the latter case, presented to a patient, the image must be digitally manipulated for precision, clarity and resolution. As a consequence, the x-ray technician is forced to take several additional steps in obtaining an adequate image. Generally, the technician first activates the x-ray source from a control room usually outfitted with radiation attenuating materials. A display unit, depending on the individual office configuration, may or may not be situated in the same x-ray control room. In any case, the technician is forced to leave the control post, operate the display unit, usually a personal computer, and retrieve and adjust the digital image. In many instances, however, the first take does not suffice, requiring the technician to repeat the procedure until a usable image is obtained. This process leads to inefficiencies and decreased productivity in the dental office, as well as increased exposure of patients to x-radiation.

Therefore, a need exists for a practical digital x-ray system and method of application in which radiation sensing elements disposed in or about a CCD sensor are no longer required. A need also exists for a system and method of obtaining dental radiographs without exposing young patients to superfluous radiation. Finally, a need exists for a system and method for providing technicians with the ability to capture, view, and manipulate digital radiographs without having to leave their post.

SUMMARY OF THE INVENTION

It is thus an object of the present invention to provide an integrated digital x-ray system for dental radiography which overcomes the drawbacks of the prior art.

It is another object of the present invention to provide an integrated digital x-ray system which provides electronic signal transduction of the exposure settings of the x-ray source, thereby eliminating the need for radiation sensors disposed in or about the image detector and substantially increasing the quality of the x-ray images as a result of a reduction of noise accumulating in the detector prior to the activation of the x-ray source.

It is yet another object of the invention to provide a system and method for taking digital radiographs whereby pre-determined exposure times are provided to the system based on certain characteristics of a patient's anatomy, thereby tailoring the exposure to the particular patient.

It is still another object of the invention to provide a system and method of displaying the processed x-ray images in accordance with the invention to allow technicians to efficiently capture, view and manipulate the images without having to leave their post, thereby increasing the productivity and workflow efficiency of the dental office.

According to the present invention, there is provided an integrated digital x-ray diagnostic system and a method for conducting dental radiography which includes optimizing exposure settings based on certain physical parameters of a patient, communicating the operational status of the x-ray generator and the exposure settings directly to an image sensor, preferably a CCD (Charged-Coupled Device), without the need for radiation sensitive detector elements or for numerous viewing stations to view image data.

Such an integrated digital x-ray diagnostic system provides an x-ray source for generating x-rays, and a source control unit connected to the x-ray source which controls the operation of the x-ray source and communicates the exposure settings of the x-ray source. A control panel is operated by a technician, thus providing the exposure settings to the source control unit. An image sensor is positioned opposite the x-ray source for receiving x-radiation passed through a patient and for delivering an analog output x-ray image of the patient. A sensor processor is coupled to the image sensor for receiving the analog output x-ray image from the image sensor and interfacing with the source control unit for receiving the exposure settings of the x-ray source. The invention also includes a converter for converting the analog output x-ray image received from the image sensor to a digital format image. The digital format image is then stored. A calibrator is also supplied for determining the x-ray exposure settings based on certain physical parameters of the patient. Finally, the invention may include a series of display units, one being preferably arranged on the control panel for viewing and manipulating the received digital images in real time.

Various other features, objects, and advantages of the invention will be made apparent to those skilled in the art from the accompanying drawings and detailed description thereof.

BRIEF DESCRIPTION OF THE DRAWINGS

FIG. 4 is a graph illustrating a prior art method of preparing the sensor to receive radiation from the x-ray source; and FIG. 5 is a graph illustrating a method of preparing the sensor to receive radiation from the x-ray source according to a preferred embodiment of the invention.

DETAILED DESCRIPTION OF THE PRESENT INVENTION

The present invention discloses a system and method for efficiently integrating x-ray generation and detection techniques. The system provides the ability to calculate and communicate the optimal radiation settings of a certain category and opacity of tooth in consideration of the specific physical anatomy of the subject patient. The system provides an arrangement whereby each component is electronically coupled to its corresponding functional mate providing for efficient signal transduction and communication of the exposure times to both the image sensor and x-ray source thereby coordinating their respective activities without the need for separate radiation sensing components. The system further provides the ability to view and manipulate the captured images at the point of x-ray source initiation.

In the following description, for purposes of explanation, numerous details are set forth in order to provide a thorough understanding of the present invention. However, it will be apparent to one skilled in the art that these specific details are not required in order to practice the present invention. In other instances, well known structures such as electronic connections are shown in block diagram form in order not to obscure the present invention.

Figure 1:
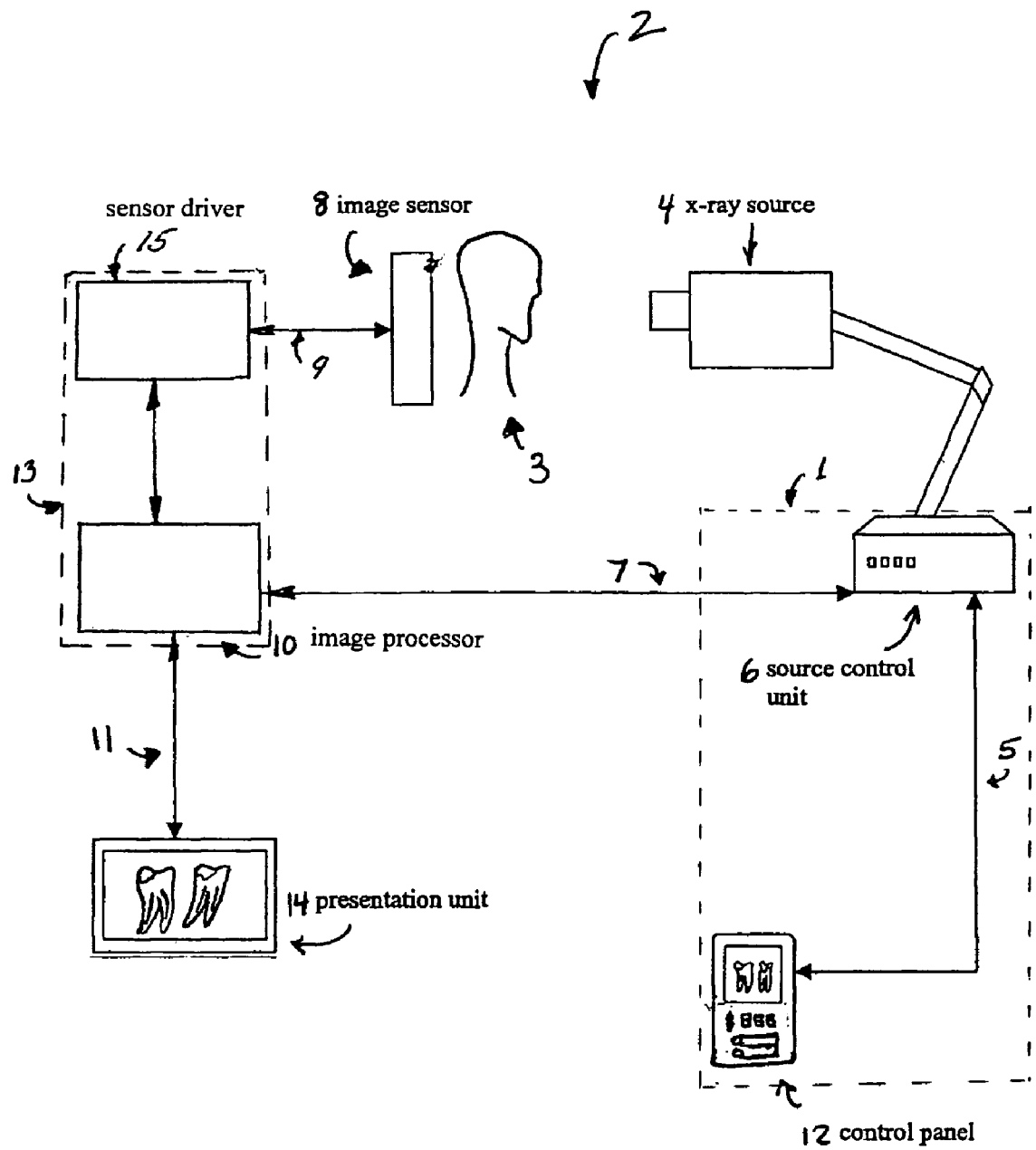
FIG. 1 is a block diagram illustration of one embodiment of a system that operates in accordance with the teachings of the present invention.

Referring now to FIG. 1, the invention provides a system 2 that includes an x-ray source 4, which provides a highly focused x-ray beam to penetrate through a patient 3. The x-ray source 4 is positioned by a dental technician in a manner to direct the radiation toward a selected area of the mouth of the patient. The x-ray source 4 is operably connected to a source control unit 6 which controls the operation of the x-ray source and performs the role of communication medium for signals originating both in a control panel 12 and an image processor 10. The source control unit 6 communicates with the control panel 12 through any suitable connection such as a wireless connection or an electronic line connection 5, and to the image processor 10 again through any suitable communication connection such as a wireless connection or an electronic line connection 7. The source control unit 6 and the control panel 12 can be housed in a single enclosure 1 or can be detachable in order to enable remote operation. The image sensor 8 is coupled to a sensor driver 15 by any suitable means, including a wireless connection or an electronic line connection 9. The sensor driver 15 is connected to the image processor 10. Very often the sensor driver 15 and the image processor 10 can be integrated or presented as a single unit 13. Alternatively the functions of the image processor 10 can be performed from available computing devices such as desktop computers, tablet PCs, laptops and PDAs. Finally, the presentation unit 14 is coupled to the image processor 10 through a wireless or wired electronic line connection 11. Preferably, each of the electronic connections provide bi-directional signal transmission.

As indicated above, the source control unit 6 is operably engaged to the x-ray source 4 and is electronically coupled to both the control panel 12 and the image processor 10. The control panel 12, in one embodiment, generates pre-determined exposure parameters and information, including time and intensity (hereinafter, "settings") that permit the synchronization of the operation of the x-ray source 4 and the image sensor 8. The control panel 12 is equipped with control buttons 16 for manual entry of exposure settings based on a library of exposure settings determined to be optimal for a certain category of tooth and physical anatomy of the patient 3. The control panel 12 is usually placed in an area or room provided with radiation attenuating properties. Once the source control unit 6 receives the exposure settings, it simultaneously redirects the settings to both the x-ray source 4 and the image processor 10. The image processor 10 then transmits the exposure settings to the image sensor 8, causing the image sensor 8 to charge in anticipation of the activation of the x-ray source 4.

The image sensor 8 is positioned opposite the x-ray source 4 and detects two-dimensionally an x-ray image, as the x-rays pass through the patient 3, as a slit image which is vertically elongated. The image sensor 8 then converts the image into electrical signals. A well-known x-ray image sensor 8 such as a CCD (Charge Coupled Device) or a CMOS (Complementary Metal Oxide Silicon) sensor is preferably used to capture the image. The image sensor 8 preferably includes a scintillator, which converts an x-ray into visible light, and a semiconductor device, which converts an image formed on the scintillator into electrical signals with a high sensitivity. The advantage in having the image sensor 8 receive an exposure signal lies in the fact that conventional CCD devices need to be in a charged state so that they are in constant readiness for incoming radiation. The use of CCDs in such a perpetual state of charge leads to increased noise accumulation along an unregulated exposure integration cycle, which detrimentally affects the quality of the resultant image. By receiving a signal as to when the x-ray source 4 is to be activated, along with the information as to the length of exposure and any other information comprising the settings, the image sensor 8 is able to provide the best quality images requiring neither perpetual charging nor radiation sensing elements disposed about the sensor.

The image processor 10 receives the analog output signal generated by the image sensor 8 through line connection 9, converts the output into a digital value for each image pixel, and formats the digital pixels into a digital image format. Preferably, the image processor 10 is a personal computer equipped with mass storage to store data and display the images on a monitor. The image processor 10 also has a built-in modem, wireless or wired network interface, or other communication device capable of transmitting the digital images to a remote location for inspection of the images. Conversion and manipulation of the images obtained using the system of the present invention is controlled by a software program in the image processor 10, preferably a digital detection software program, designed in the preferred embodiment to operate in the Microsoft Windows® environment but not excluding other operating systems as Linux®, Unix®, or Palm®, among others. Manipulation functions may include, but are not limited to, the modification of the displayed contrast, magnification of the displayed image, digital stretching, sharpening of the image, point-to-point measurements, annotation of the image, storage and retrieval of stored images, and correction of the orientation of the image to correct for differing operating positions of the image sensor 8. In the preferred embodiment as shown in FIG. 1, the image processor 10 is equipped to electronically communicate image data to the source control unit 6 which then relays the image data to the control panel 12 for display. In another embodiment, the image processor 10 may communicate directly with the control panel 12. In a still another embodiment of the present invention, the image processor 10 may be configured and positioned in a manner to present the displayed image to the patient.

As indicated above, presentation unit 14 is also shown in FIG. 1 coupled to the image processor 10 through connection 11. The presentation unit 14 receives the formatted images from the image processor 10 and may take the form of a personal computer, a flat solid state digital display panel, or a conventional CRT with a digital signal converter. The presentation unit 14 is preferably employed in a separate office away from the x-ray source 4 and is preferably capable of displaying the full dynamic range and resolution of the image sensor 8. In another embodiment, the presentation unit 14 may be integrated in such a manner that the image processor software may operate within the presentation unit 14 to allow for the manipulation and storage of the images.

Figure 2:
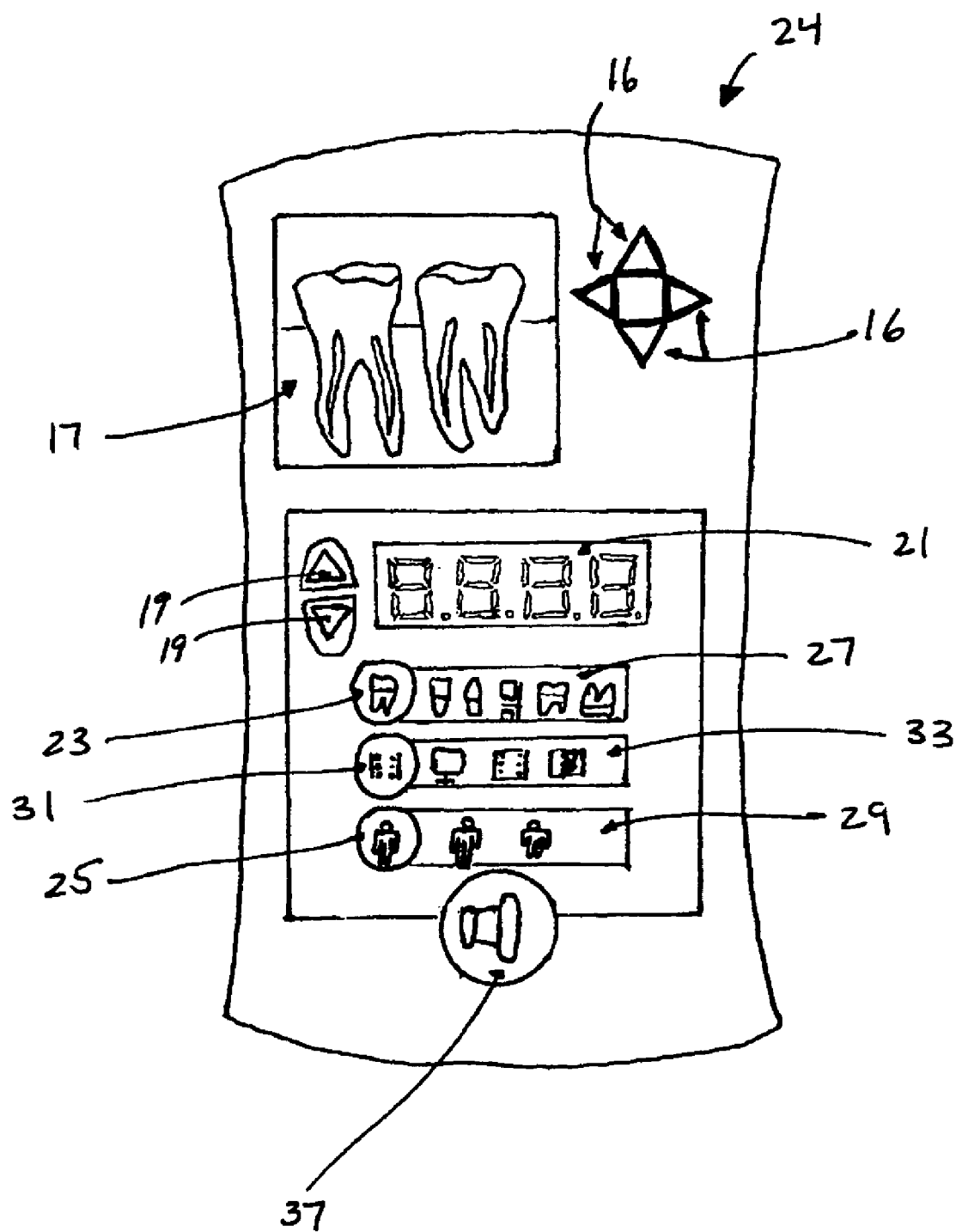
FIG. 2 is a top plan view of an embodiment of a control panel that is part of the system of the present invention.

FIG. 2 shows control panel 24, which may be similar in functionality to control panel 12, in accordance with another embodiment of the present invention. The control panel 24 of the present embodiment comprises an intelligent display unit or PDA-type device with a flat solid state display 17 for the presentation of images received from the image processor 10. A PDA or Personal Digital Assistant is a pocket-sized personal computer which is typically used to store phone numbers, appointments, and to-do lists. Some PDAs have a small keyboard, whereas others have only a special stylus that is used for input on a touch sensitive screen. A PDA can also have a wired or wireless network adapter or a wired or wireless modem, including a fax modem. Files can be created on a PDA which are later entered or transferred into a larger computer.

An arrangement which incorporates a PDA-type device provides portability of the displayed image, supplying the technician with the ability to physically transfer the diagnosis quality radiograph anywhere the dentist is located at any given moment. Additionally, the control panel 24 can be networked to other computers via any suitable network or communications interface (e.g. wired or wireless Ethernet or USB). This arrangement allows the technician to transfer images to remote computers where they can be additionally modified or stored in a standard database or a specific patient's file.

Image processor software similar in features and functions to those described above for the image processor 10 may be provided in the control panel 24 to provide manipulation functions including but not limited to modifying the displayed contrast, adjusting the magnification and brightness of the displayed image, and sharpening of the image. A set of function buttons 16, preferably located beside the display panel 17, are used to access some of the processing features of the control panel 24. These function buttons 16 may allow the technician to manually enter a known exposure setting, which may then be reflected in the digital number display 21 adjacent to additional function buttons 19, which allow a user to change certain parameters. The control panel 24 may also include a series of parameter buttons 23, 31, 25, including one 23 for a selection panel 27 representing each category and orientation of tooth types to be irradiated. Another parameter button 25, which corresponds to selection panel 29, may be used to enter the physical size of the patient, or to select a size from a list provided. The technician, depending on which category of tooth is to be examined, enters a specific tooth anatomy from the listed selection panel 27 by selecting the desired category and orientation as indicated on the panel. Similarly, depending on the physical maturity of the patient, the technician may use a parameter button to select one of the available patient sizes on selection panel 29. A calibrator, preferably in software, is supplied with the control panel 24 to calculate the optimal exposure times based on the entered anatomical parameters. This calibration software matches the entered exposure parameters to a library of known optimal exposure ranges saved in the control panel database. There may also be an operation mode button 31 that controls the status of the control panel 24 by providing a set of alternative condition modes 33. Preferably, the condition modes include: 1) a "display mode," depicted in FIG. 2 by an image of a monitor used for displaying and manipulating images; 2) a "static mode," depicted in FIG. 2 by an image of a reel of film used to set the exposure parameters; and 3) an "active mode," depicted in FIG. 2 by an image of a reel of film with a bolt of electricity disposed about the middle, to indicate that the x-ray source is activated. Other images may also be used. An exposure button 37 may be supplied so as to, when pressed, initiate the transfer of the exposure settings.

Figure 3:
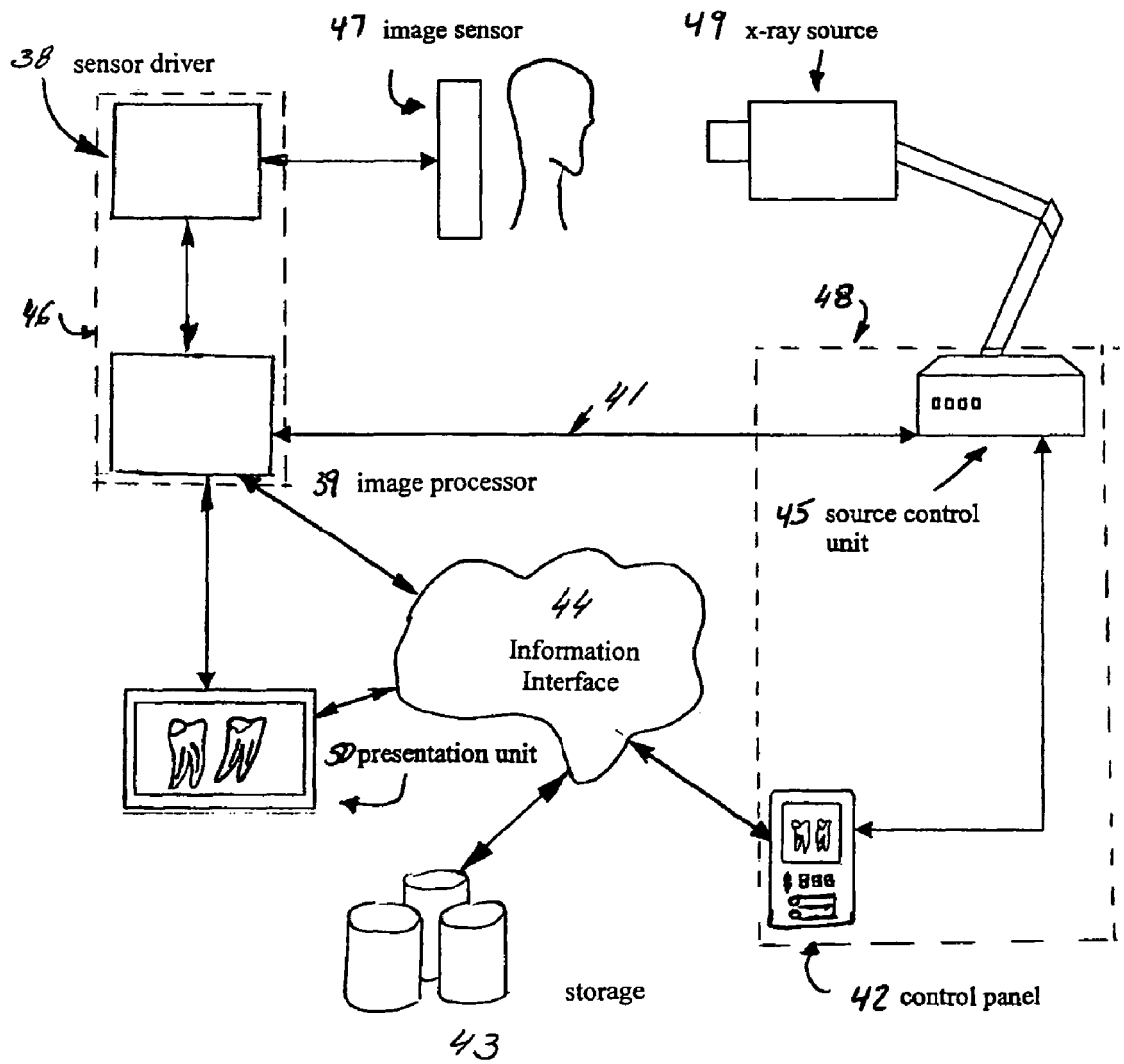
FIG. 3 is a block diagram illustration of another embodiment of a system that operates in accordance with the teachings of the present invention.

Referring now to FIG. 3, in yet another embodiment of the present invention, the calibration software is run in an image processor 39 rather than the control panel. The image processor 39 is coupled and communicates with a control panel 42 through an information interface 44 or a local connection 41. The information interface 44 can be any commercial interface as DICOM or private developed communication interface or other compilation of control, acquisition and communication interfaces. To initiate the system, the technician inputs the exposure parameters as described above. However, the control panel 42 in this embodiment does not contain calibration software. Instead, the packaged exposure parameters are communicated by the control panel 42 directly to the image processor 39. The image processor 39 is additionally coupled to both the source control unit 45 and the image sensor 47 through a sensor driver 38. On receiving the exposure parameters, the image processor 39 calculates the optimal corresponding exposure times using the calibration software and then simultaneously signals both the source control unit 45 and the image sensor 47 with the exposure settings. The source control unit 45 then activates the x-ray source 49 with the pre-determined settings. After the image is captured, the image sensor 47 communicates the analog CCD image to the image processor 39 for conversion and formatting. The finished image is then communicated over the information interface 44 to either/both the remote presentation unit 50 or/and storage database 43 or/and the control panel 42 which contain the digital detection software for manipulation and display. The source control unit 45 and the control panel 42 can be housed in a single enclosure 48 or can be detachable in order to enable remote operation. The sensor driver 38 and the image processor 39 can be integrated or presented as a single unit 46.

Thus, by use of the present invention, efficient x-ray generation is achieved without pre-integration of charge in the image sensor 47, nor with over-exposure risks associated with known dental radiography techniques. This efficiency solves a problem which will be described with respect to FIGS. 4 and 5 below.

In current digital x-ray radiographic systems, noise performance is limited based on a number of factors, one important one being the manner in which the sensor detects the x-radiation. Generally, the incoming x-radiation is converted to visible light and then is applied to silicon structure of either a CMOS or CCD sensor. The light changes the charge of the small virtual capacitors within the silicon structure, and this charge is then transferred and transformed into an electrical signal. To be successful, this process requires initial "cleaning" of the signal charge in the silicon structure. Referring now to FIG. 4, this cleaning process is referred to as "Preparation." After the Preparation step, the sensor waits for x-radiation. During most of this waiting time, the sensor does not acquire additional noise. When the x-ray source is activated, the sensor then goes into an Integration Phase and accumulates the x-ray signal. When the x-ray source is deactivated, the sensor can read the accumulated x-ray image during the Read Phase. The biggest problem with this process is that of reliably determining when the Integration Phase should start and when it should stop. If the Integration Phase is active when the x-ray source is not active, the sensor will accumulate extra dark current noise. Conversely, if the sensor is not in its Integration Phase when the x-ray source is activated, the sensor will lose some of the useful energy for forming an image, but worse than that, it can smear the resultant image.

FIG. 5 shows graphically the result of the present invention. As can there be seen, the sensor is activated with the x-ray source, and deactivated in synchronization with the x-ray source. This synchronization produces substantially reduced smearing, and substantially reduced dark current noise, resulting in a clearer image with less unnecessary x-ray exposure for the patient.

The provision of the digital processors and storage by this invention permits another important benefit. Given that the amount of radiation received by the sensor can be known, and the amount of radiation emitted by the x-ray source can be known, it can then be calculated how much exposure a particular patient is receiving any time an x-ray is taken. This exposure information can then be stored for that patient over time, enabling a health care provider to maintain a long term record of x-ray exposure for each patient.

From the foregoing, it can be appreciated that the present invention reliably provides for the accomplishment of the objects of the invention and does so in a particularly simple and economical manner. It is recognized, of course, that those skilled in the art may make various modifications or additions to the preferred embodiments chosen to illustrate the invention without departing from the spirit and scope of the invention itself. Accordingly, it is to be understood that the invention should be deemed to extend to the subject matter claimed and all equivalents thereof fairly within the scope of the claims.

What is claimed is:

1. An integrated digital x-ray imaging system for dental radiography, comprising:
   an x-ray source;
   a source control unit operably connected to the x-ray source which controls operation of the x-ray source and exposure settings of the x-ray source;
   a control panel coupled to the source control unit which provides the exposure settings to the source control unit;
   an image sensor positioned for receiving x-ray radiation from the x-ray source passed through a patient, and for delivering an analog output x-ray image of the patient;
   a sensor driver coupled to the image sensor receiving the analog output x-ray image from the image sensor;

an image processor coupled to the sensor driver for converting the analog output x-ray image received from the image sensor to a digital format image and for processing the digital format image, wherein the image processor interfaces with the source control unit for receiving the exposure settings of the x-ray source; and a display for presenting the digital format image.

2. The digital x-ray imaging system of claim 1 wherein the exposure settings comprise pre-determined x-ray exposure times based on the category of tooth and the physical size of the patient.

3. The digital x-ray imaging system of claim 2 further comprising a calibrator for calculating the exposure settings based on certain anatomical parameters of the patient.

4. The digital x-ray imaging system of claim 3 wherein the anatomical parameters used for calculating exposure times are based on the category of tooth and the physical size of the patient.

5. The digital x-ray imaging system of claim 4 wherein the image sensor is a CCD or CMOS x-ray image detector.

6. The digital x-ray imaging system of claim 5 wherein the display is a personal computer monitor, a flat panel display, or a television.

7. The digital x-ray imaging system of claim 6 wherein an additional display is coupled to the image processor.

8. The digital x-ray imaging system of claim 7 wherein the display is a flat panel display located on the control panel.

9. The digital x-ray imaging system of claim 8 wherein the control panel is a portable PDA-type device.

10. The digital x-ray imaging system of claim 9 wherein the image processor comprises digital detection software supplied with the image processor.

11. An integrated digital x-ray imaging system for dental radiography, comprising:

an x-ray source;

a source control unit operably connected to the x-ray source which controls operation of the x-ray source and signals pre-determined x-ray exposure times based on the category of tooth and the physical size of a patient and displays an x-ray image;

a control panel coupled to the source control unit which provides exposure settings to the source control unit and comprises a PDA-type device with a flat panel display;

a CCD image sensor positioned to receive x-ray radiation from the x-ray source passed through the patient, and for delivering an analog output x-ray image of the patient;

a sensor driver coupled to the image sensor receiving the analog output x-ray image from the image sensor;

a calibrator capable of calculating the exposure settings based on the category of tooth and the physical size of the patient;

an image processor coupled to the sensor driver and the control panel for converting the analog output x-ray image received from the image sensor to a digital format image and for processing the digital format image, wherein the image processor interfaces with the source control unit for receiving the exposure settings of the x-ray source; and a display unit for presenting the digital format image.

12. A method for performing dental radiography on a patient, the method comprising the steps of:

arranging an x-ray source in a desired location, in relation to the mouth of the patient to be irradiated, and opposite an image sensor;

activating the x-ray source and the image sensor in a coordinated manner, so as to avoid pre-integration of charge in the image sensor, and at the same time reduce risk of over-exposure;

coupling a sensor driver and an image processor to the image sensor for receiving an analog output x-ray image from the image sensor and converting the analog output x-ray image to a digitally formatted x-ray image, wherein the image processor interfaces with a source control unit for receiving exposure settings from the x-ray source; and receiving the digitally formatted x-ray image from the image processor at a control panel which provides the exposure settings to the source control unit.

13. The method as recited in claim 12, further comprising the steps of viewing the x-ray image from the control panel;

manipulating the x-ray image to provide a diagnosis quality image; and storing the x-ray image.

14. The method as recited in claim 13 further comprising the step of measuring an exposure rate and calculating a dosage for each of multiple x-ray pictures or series.

15. A method for performing dental radiography on a patient, the method comprising the steps of:

placing the patient in a dental chair, and arranging an x-ray source in a desired locations in relation to the mouth to be irradiated and opposite an image sensor;

activating the x-ray source;

coupling a sensor driver and an image processor to the image sensor for receiving an analog output x-ray image from the image sensor and converting the analog output x-ray image to a digitally formatted x-ray image wherein the image processor interfaces with a source control unit for receiving exposure settings from the x-ray source;

receiving the digitally formatted x-ray image from the image processor at a control panel which provides the exposure settings to the source control unit;

viewing the x-ray image from the control panel;

manipulating the x-ray image to provide a diagnosis quality image;

storing the x-ray image; and measuring an exposure rate and calculating a dosage for each of multiple x-ray pictures or series.

16. The method of claim 15 further comprising the step of providing the control panel in a remote area, and wherein the control panel is a portable PDA-type x-ray control panel supplied with a flat panel digital display and image manipulation software.

17. The method of claim 16 further comprising the step of removing the control panel from its station to a different area of a dental office.

18. The method of claim 16 wherein the step of activating the x-ray source is accomplished by pressing an exposure button located on the control panel.

19. The method of claim 16 wherein the x-ray image is sent via a network connection to a storage database.

20. The method of claim 15 wherein the x-ray image is manipulated for contrast, clarity, brightness, resolution, and accuracy.

* * * * *